United States Patent
Haiminen et al.

(10) Patent No.: US 11,177,018 B2
(45) Date of Patent: *Nov. 16, 2021

(54) STABLE GENES IN COMPARATIVE TRANSCRIPTOMICS

(71) Applicant: International Business Machines Corporation, Armonk, NY (US)

(72) Inventors: Niina S. Haiminen, White Plains, NY (US); Laxmi P. Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 615 days.

This patent is subject to a terminal disclaimer.

(21) Appl. No.: 16/114,598

(22) Filed: Aug. 28, 2018

(65) Prior Publication Data
US 2018/0365378 A1 Dec. 20, 2018

Related U.S. Application Data

(63) Continuation of application No. 13/713,970, filed on Dec. 13, 2012, now Pat. No. 10,083,275.

(51) Int. Cl.
*G16B 30/00* (2019.01)
(52) U.S. Cl.
CPC ................... *G16B 30/00* (2019.02)
(58) Field of Classification Search
None
See application file for complete search history.

(56) References Cited

U.S. PATENT DOCUMENTS

| | | | |
|---|---|---|---|
| 6,571,230 B1 | 5/2003 | Parida | |
| 7,617,054 B2 | 11/2009 | Sayer et al. | |
| 7,797,326 B2 | 9/2010 | Goplan et al. | |
| 7,991,709 B2 | 8/2011 | Dejean et al. | |
| 2003/0215807 A1 | 11/2003 | Wolber et al. | |
| 2005/0159898 A1 | 7/2005 | Yasuda et al. | |
| 2005/0181399 A1 | 8/2005 | Okimoto et al. | |
| 2006/0136145 A1 | 6/2006 | Kao | |
| 2006/0292610 A1 | 12/2006 | Shen et al. | |
| 2007/0161009 A1 | 7/2007 | Kohne | |
| 2008/0234138 A1 | 9/2008 | Shaughnessy et al. | |
| 2009/0099034 A1 | 4/2009 | Ahlquist et al. | |
| 2010/0146517 A1 | 6/2010 | Aschen et al. | |
| 2010/0166716 A1 | 7/2010 | Serikov et al. | |
| 2011/0004415 A1 | 1/2011 | Miyake et al. | |
| 2011/0004416 A1 | 1/2011 | Apostolico et al. | |
| 2011/0131170 A1 | 6/2011 | Golab et al. | |
| 2011/0225109 A1 | 9/2011 | Burns et al. | |

OTHER PUBLICATIONS

Non-Final rejection for U.S. Appl. No. 13/713,970 dated Sep. 16, 2015 dated Sep. 16, 2015.
Final rejection for U.S. Appl. No. 13/713,970 dated Jan. 20, 2017 dated Jan. 20, 2017.
Final Office Action dated Feb. 16, 2016 received for U.S. Appl. No. 14/030,675, dated Feb. 16, 2016.
Enslow (Computer (Jan. 1978) Reader Service No. 2, pp. 13-21 Jan. 1978.
Srimani et al. (IEEE Intl. Conf, on Bioinformatics and Biomedicine Workshops (2010):579-584) 2010.
Non-Final Office Action dated Sep. 17, 2015 received for U.S. Appl. No. 14/030,675, dated Sep. 17, 2015.
Lemire, D., "A Better Alternative to Piecewise Linear Time Series Segmentation", SDM, Apr. 2007, pp. 1-12. Apr. 2007.
Skiena, S., "The Algorithm Design Manual", Second Edition, Springer-Verlag, Jul. 2008, pp. 1-46. Jul. 2008.
Bullard, J., et al., "Evaluation of Statistical Methods for Normalization and Differential Expression in mRNA-Seq Experiments", BMC Bioinformatics, Feb. 2010, pp. 1-13, vol. 11, No. 94. Feb. 2010.
Dohm, J., et al., "Substantial Biases in Ultra-Short Read Data Sets From High-Throughput DNA Sequencing", Nucleic Acids Research, Jul. 26, 2008, pp. 1-10, vol. 36, No. 16. Jul. 26, 2008.
Cheng, C., et al., "A Statistical Framework for Modeling Gene Expression Using Chromatin Features and Application to modENCODE Datasets", Genome Biology, Feb. 2011, pp. 1-18, V12, R15. Feb. 2011.
Wu, B., "Differential Gene Expression Detection and Sample Classification Using Penalized Linear Regression Models", Bioinformatics, Dec. 2005, pp. 472-476, vol. 22, No. 4. Dec. 2005.
Mortazavi, A., et al., "Mapping and Quantifying Mammalian Transcriptomes by RNA-Seq", Nature Methods, Jul. 2008, pp. 621-628, vol. 5. Jul. 2008.
Jiang, H., et al., "Statistical Inferences for Isoform Expression in RNA-Seq", Bioinformatics, Feb. 2009, pp. 1026-1032, vol. 25, No. 8. Feb. 2009.
Hansen, K., et al., "Biases in Illumina Transcriptome Sequencing Caused by Random Hexamer Priming", Nucleic Acids Research, Published online Apr. 14, 2010, pp. 1-7, vol. 38, No. 12. Apr. 2010.
Trapnell, C., et al., "Transcript Assembly and Quantification by RNA-Seq Reveals Unannotated Transcripts and Isoform Switching During Cell Differentiation", Nature Biotechnology, May 2010, pp. 1-8, vol. 28, No. 5. May 2010.
Robinson et al. (Genome Biology (2010) vol. 11, R25, pp. 1-9) 2010.

(Continued)

*Primary Examiner* — Lori A. Clow
(74) *Attorney, Agent, or Firm* — Fleit Intellectual Property Law; Thomas S. Grzesik (57) ABSTRACT

Various embodiments perform stable gene analysis of transcriptome sequencing data. In one embodiment, a plurality of datasets each including transcriptome sequencing data are received by a processor. Each of the plurality of datasets includes a plurality of genes and a respective ranking value for each of the plurality of genes. A plurality of rank normalized input datasets is generated based on assigning, for each of the plurality of datasets, a rank to each of the plurality of genes. One or more longest increasing subsequence (LIS) of ranks are identified between each pair of the plurality of rank normalized input datasets. A set of stable genes from the plurality of genes is identified based on each of the one or more LIS of ranks across the plurality of rank normalized input datasets.

19 Claims, 5 Drawing Sheets

(56) References Cited

OTHER PUBLICATIONS

Kroll et al. (Nucleic Acids Research (2002) vol. 30, e50; pp. 1-6) 2002.
Zhang et al. (Bioinformatics (2003) vol. 19, pp. 1391-1396) 2003.
Li, F., Xu, W., Li, P. et al. (Oct. 2009). Optimizing reference gene set for inter-chip normalization using genetic algorithm. 2009 2nd International Conference on Biomedical Engineering and Informatics, BMEI '09, 1-4. 2009.
Lei, Y., Han, Y., Berens, M. E. (Feb. 2012). Stable gene selection from microarray data via sample weighting. IEEE/ACM Transactions on Computational Biology and Bioinformatics, 9(1), 262-272. 2012.
Wang, Q., Korkin, D., Shang, Y. (Mar. 2011). A fast Multiple Longest Common Subsequence (MLCS) algorithm. IEEE Transactions on Knowledge and Data Engineering, 23(3), 321-334. 2011.
Truntzer C. Maucort-Boulch, D., Roy, P. (Oct. 2008). Comparative optimism in models involving both classical clinincal and gene expression information. BMC Bioinformatics, 9(434). Oct. 2008, 10 pages.

STABLE GENES IN COMPARATIVE TRANSCRIPTOMICS

BACKGROUND

The present invention generally relates to the field of computational biology, and more particularly relates to stable gene analysis of transcriptome sequencing data.

Transcriptome data, including messenger riboneucleic acid (mRNA) data, may arise from genes, and more specifically from gene transcripts. A gene may have multiple differently spliced transcripts that give rise to mRNAs, and mRNAs may also arise from other regions on the genome. Sequencing technologies may provide data for a wide range of biological applications, and are powerful tools for investigating and understanding mRNA expression profiles. There is no limit on the number of mRNAs that may be surveyed by sequencing. Sequencing may not be target specific, so the genes that are examined do not have to be pre-selected, providing a wide dynamic range of data and also allowing the possibility of discovering new sequence variants and transcripts.

Various sequencing platforms may be used to perform mRNA sequencing and to produce mRNA sequencing datasets, each dataset corresponding to an assay of a particular sample. Such mRNA sequencing technologies may be high-throughput and produce relatively large amounts of sequence data. The size of an mRNA sequencing dataset may require the use of various computational techniques to make accurate and meaningful inferences regarding sequenced mRNAs from the dataset. In addition, datasets from different assays (which may be from the same sample at different points in time or from different samples) may also need to be compared. Analyzing data regarding relatively large numbers of mRNAs based on their activity, or expression, levels across different assays may be a complex process.

BRIEF SUMMARY

In one embodiment, a computer implemented method for performing stable gene analysis of transcriptome sequencing data is disclosed. The computer implemented method includes obtaining, by a processor, a plurality of datasets each including transcriptome sequencing data. Each of the plurality of datasets includes a plurality of genes and a respective ranking value associated with each of the plurality of genes. A plurality of rank normalized input datasets is generated based on assigning, for each of the plurality of datasets, a rank to each of the plurality of genes. One or more longest increasing subsequences of ranks are identified between each pair of the plurality of rank normalized input datasets. A set of stable genes from the plurality of genes is identified based on each of the one or more longest increasing subsequences of ranks across the plurality of rank normalized input datasets.

In another embodiment, an information processing system for performing stable gene analysis of transcriptome sequencing data is disclosed. The information processing system includes a memory and a processor that is communicatively coupled to the memory. A transcriptome sequencing data analyzer is communicatively coupled to the memory and the processor. The transcriptome sequencing data analyzer is configured to perform a method. The method includes obtaining, by a processor, a plurality of datasets each including transcriptome sequencing data. Each of the plurality of datasets includes a plurality of genes and a respective ranking value associated with each of the plurality of genes. A plurality of rank normalized input datasets is generated based on assigning, for each of the plurality of datasets, a rank to each of the plurality of genes. One or more longest increasing subsequences of ranks are identified between each pair of the plurality of rank normalized input datasets. A set of stable genes from the plurality of genes is identified based on each of the one or more longest increasing subsequences of ranks across the plurality of rank normalized input datasets.

In a further embodiment, a non-transitory computer program product for performing stable gene analysis of transcriptome sequencing data is disclosed. The computer program product includes a storage medium readable by a processing circuit and storing instructions for execution by the processing circuit for performing a method. The method includes obtaining, by a processor, a plurality of datasets each including transcriptome sequencing data. Each of the plurality of datasets includes a plurality of genes and a respective ranking value associated with each of the plurality of genes. A plurality of rank normalized input datasets is generated based on assigning, for each of the plurality of datasets, a rank to each of the plurality of genes. One or more longest increasing subsequences of ranks are identified between each pair of the plurality of rank normalized input datasets. A set of stable genes from the plurality of genes is identified based on each of the one or more longest increasing subsequences of ranks across the plurality of rank normalized input datasets.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present invention, in which.

DETAILED DESCRIPTION

Figure 1:
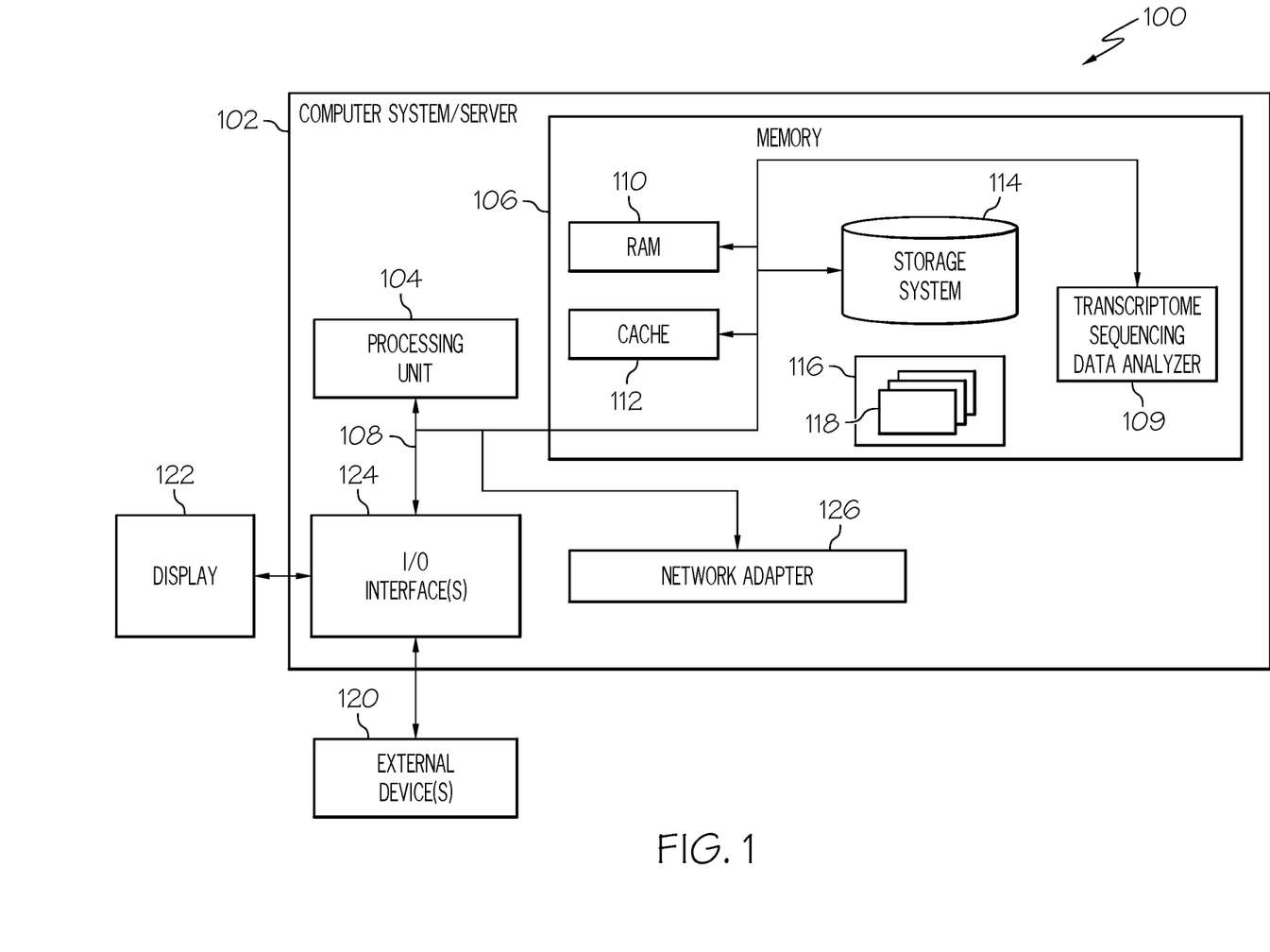
FIG. 1 is a block diagram illustrating one example of an operating environment according to one embodiment of the present invention.

FIG. 1 illustrates a general overview of one operating environment 100 for stable gene analysis of transcriptome sequencing data according to one embodiment of the present invention. In particular, FIG. 1 illustrates an information processing system 102 that can be utilized in embodiments of the present invention. The information processing system 102 shown in FIG. 1 is only one example of a suitable system and is not intended to limit the scope of use or functionality of embodiments of the present invention described above. The information processing system 102 of FIG. 1 is capable of implementing and/or performing any of the functionality set forth above. Any suitably configured processing system can be used as the information processing system 102 in embodiments of the present invention.

As illustrated in FIG. 1, the information processing system 102 is in the form of a general-purpose computing device. The components of the information processing system 102 can include, but are not limited to, one or more processors or processing units 104, a system memory 106, and a bus 108 that couples various system components including the system memory 106 to the processor 104.

The bus 108 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The system memory 106, in one embodiment, includes a transcriptome sequencing data analyzer 109 configured to at least identify stable genes from transcriptome sequencing data. For example, the transcriptome sequencing data analyzer module 109, in one embodiment, takes as input two or more datasets, respectively, for a gene, a gene transcript, or an mRNA, etc. These datasets include expression levels for each gene in the gene set associated with the assays. In one embodiment, the datasets include at least two real measured datasets. These can be biological or technical replicates (to address stability of the sequencing technology), or the datasets can be from completely different samples. The transcriptome sequencing data analyzer module 109 can generate simulated replicate datasets for more robust discovery of stable genes for each of the at least two input datasets. Alternative, the transcriptome sequencing data analyzer module 109 can use ranks provided as input for the at least two input datasets (without real or simulated replicates).

The transcriptome sequencing data analyzer 109 performs rank normalization of the gene expression level/abundance of the input datasets. In another embodiment, the transcriptome sequencing data analyzer 109 performs rank normalization of datasets generated by repeated sampling from the expression level/abundance distribution of the input datasets. It should be noted that rank normalized data can also be provided as input to the transcriptome sequencing data analyzer 109. A set of genes with a longest increasing subsequence (LIS) of ranks between rank normalized input datasets, or between rank normalized sampled instances of input datasets is determined/identified. The transcriptome sequencing data analyzer 109 then selects a set of stable genes that are present in the B longest increasing subsequences between rank normalized input datasets, or between rank normalized sampled instances of input datasets.

It should be noted that the transcriptome sequencing data analyzer 109 can be a standalone module, a part of simulator, etc. Also, even though FIG. 1 shows the transcriptome sequencing data analyzer 109 residing in the main memory, the transcriptome sequencing data analyzer 109 can reside within the processor 104, can be distributed across a plurality of information processing systems and/or processors, or can a separate hardware component. The system memory 106 can also include computer system readable media in the form of volatile memory, such as random access memory (RAM) 110 and/or cache memory 112.

The information processing system 102 can further include other removable/non-removable, volatile/non-volatile computer system storage media. By way of example only, a storage system 114 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 108 by one or more data media interfaces. The memory 106 can include at least one program product having a set of program modules that are configured to carry out the functions of an embodiment of the present invention.

Program/utility 116, having a set of program modules 118, may be stored in memory 106 by way of example, and not limitation, as well as an operating system, one or more application programs, other program modules, and program data. Each of the operating system, one or more application programs, other program modules, and program data or some combination thereof, may include an implementation of a networking environment. Program modules 118 generally carry out the functions and/or methodologies of embodiments of the present invention.

The information processing system 102 can also communicate with one or more external devices 120 such as a keyboard, a pointing device, a display 122, etc.; one or more devices that enable a user to interact with the information processing system 102; and/or any devices (e.g., network card, modem, etc.) that enable computer system/server 102 to communicate with one or more other computing devices. Such communication can occur via I/O interfaces 124. Still yet, the information processing system 102 can communicate with one or more networks such as a local area network (LAN), a general wide area network (WAN), and/or a public network (e.g., the Internet) via network adapter 126. As depicted, the network adapter 126 communicates with the other components of information processing system 102 via the bus 108. Other hardware and/or software components can also be used in conjunction with the information processing system 102. Examples include, but are not limited to: microcode, device drivers, redundant processing units, external disk drive arrays, RAID systems, tape drives, and data archival storage systems.

One or more embodiments discussed below provide stable gene analysis of transcriptome sequencing data. In one embodiment, stable gene analysis is performed using rank normalization. Normalization of transcriptome sequencing data may be based on the relative placement of the genes in the dataset with respect to the other genes in the dataset. The term "gene", as used herein, may also refer to any transcriptome sequencing entity, including a transcript or mRNA in various embodiments. Rank normalization of gene data yields unit-free numbers for each gene that may be used to make comparisons across data sets. Rankings may be determined for individual genes within a dataset. The two datasets that are compared may include transcriptome sequencing data from two different samples in some embodiments, or may include transcriptome sequencing data from a single sample at two different points in time in other embodiments.

This allows the identification of stable genes across datasets without use of scaling. Rank normalization may be used in conjunction with transcriptome sequencing data obtained using any appropriate sequencing platform.

In one embodiment, the genes are ranked based on a ranking value, which is a value for which data is available in the dataset for each ranked gene. The genes may be ordered in ascending or descending order of the ranking value to produce a rank normalized dataset in various embodiments. In some embodiments, each gene in the dataset may be assigned a unique ranking. In other embodiments, the rankings may be determined based on assigning genes to bins, each bin including a range of values. Each gene assigned to the same bin is therefore assigned the same rank, and changes in bin number for a particular gene between datasets may be used to determine the differential expression of the particular gene. The range of values corresponding to each bin may be determined based on linear regression analysis of the dataset that is being rank normalized, so that the bin ranges may be tailored to the particular dataset.

In comparative transcriptomics two classes of genes are distinguished from one another: a first class whose members are differentially expressed, and a second class whose members are stable across the two samples a and b with sufficient confidence. Unfortunately, these two classes, which appear complementary in their characteristics, do not partition the genes G into two because of the need to meet confidence thresholds. Therefore, one or more embodiments provide a framework for identifying stable genes in transcriptome sequencing data.

In one embodiment of this framework, a character function $\phi_g$ is defined for each gene g instead of directly working with the expression value of the gene g. In this embodiment, the function $\phi_g$ depends on the expression values of all the other genes in the assay, and is scale invariant. With respect to notation, let $G=\{g_1, g_2, \ldots, g_L\}$ be a set of L genes. Then let an L-tuple of random variables $$T=(X_{g_1}, X_{g_2}, \ldots, X_{g_L})=(X_g)_{g\in G} \quad (EQ. 1)$$

represent a biological sample with L genes G. $X_g$ is a random variable representing the observed expression or abundance of gene g. In this model-less framework, no assumptions are made about the distribution of each of the component random variable $X_g$. Next, consider the L-tuple of random variables $$\Phi(T)=(\phi_{g_1}(T), \phi_{g_2}(T), \ldots, \phi_{g_L}(T))=(\phi_g(T))_{g\in G}, \quad (EQ. 2)$$

whose components, $\phi_g$ termed character functions, are defined below. In particular, these functions are scale invariant.

The following is a definition of the character functions. For a fixed P>1, number of target values (or bins), a surjective map $$\phi=(\phi_g)_{g\in G}:R_{\geq 0}^G \rightarrow \{1, 2, \ldots, P\} \quad (EQ. 3)$$

is referred to as a character function if there exists a P-dimensional constant $(\delta_p)_{1\leq p\leq P} \in R_{\geq 0}^P$, satisfying the following conditions for the observed abundances t of genes g:

1. if $\phi_g(t)=\phi_{g'}(t)=p$ then $|t_g-t_{g'}|\leq \delta_p$, and
2. if $\phi_g(t)<\phi_{g'}(t)$, then $t_g<t_{g'}$, for all g, g' $\in$ G, and $t=(t_g)_{g\in G} \in R_{\geq 0}^G$.

Notice that such a character function satisfies the following additional properties.

1. $\phi_g$ is scale-invariant: $\phi_g(ct)=\phi_g(t)$ for all c>0 and t $\in R_{\geq 0}^G$.

This follows from the first condition of the definition of $\phi_g$.

2. For all triplets, g, g', g", if $t_g<t_{g'}<t_{g''}$ with $\phi_g(t)=\phi_{g''}(t)$ then $\phi_g(t)=\phi_{g'}(t)=\phi_{g''}(t)$ This property follows from the second condition of the definition. This property is utilized, in one embodiment, to compute the scale-invariant maps. For two samples a and b defined on the same gene set G, let a pair of L-tuples of random variables, $T^a$ and $T^b$, represent the two samples. Let the corresponding scale-invariant character maps be $\Phi(T^a)=\Phi^a$ and $\Phi(T^b)=\Phi^b$. Recall from EQ. 3 that the image of $\phi$ is $\{1, 2, \ldots, p, \ldots, P\}$.

Figure 2:
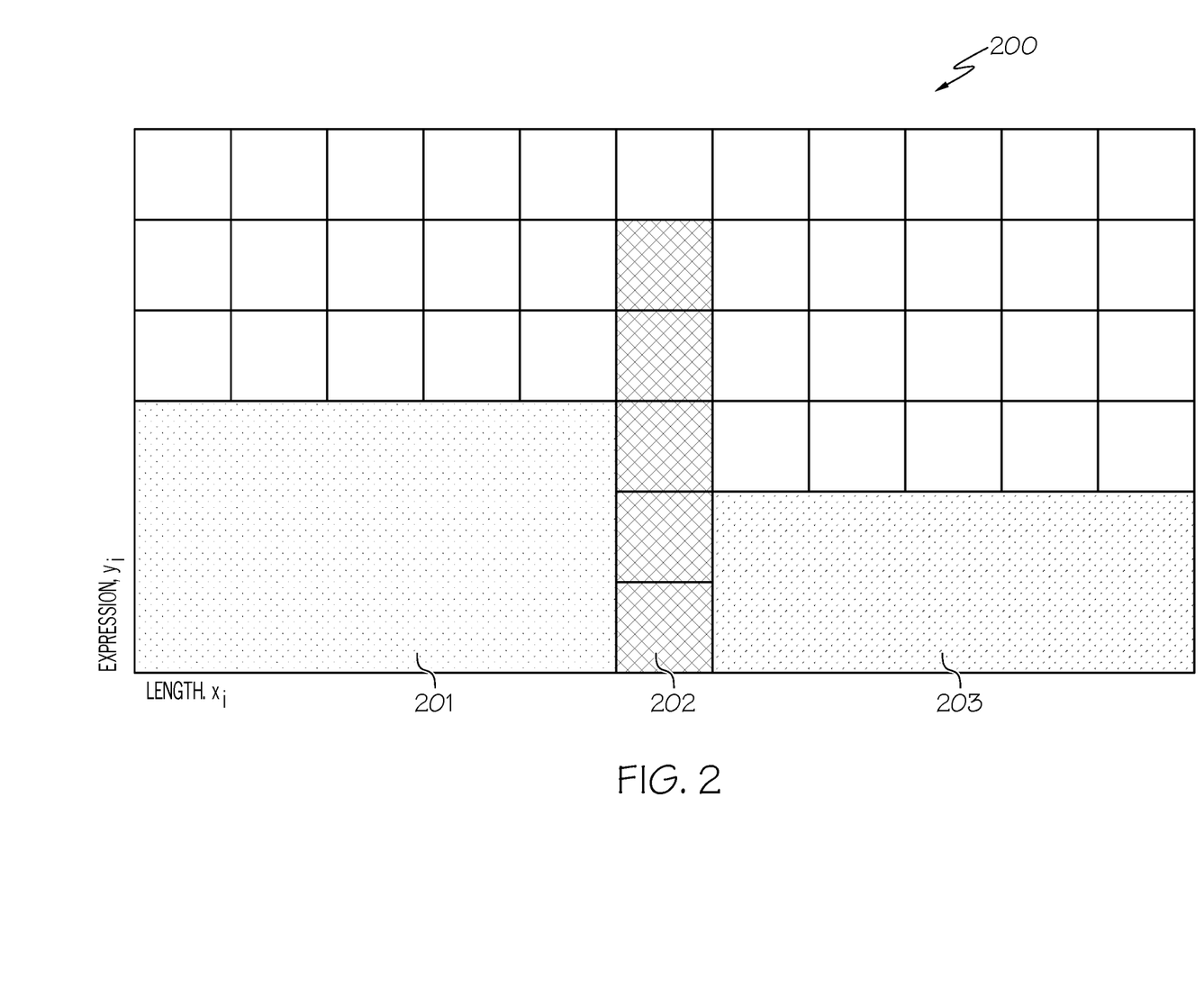
FIG. 2 illustrates a graph of gene length versus expression level for example genes in a sample according to one embodiment of the present invention.

The transcriptome sequencing data analyzer 109 utilizes the framework discussed above to perform stable gene analysis of transcriptome sequencing data. In one embodiment, the transcriptome sequencing data analyzer 109 obtains a plurality of input datasets each including genes. Each dataset may include data from assays of a single sample at different points in time, or may include data from assays of different samples. One example of an input dataset is a transcriptome sequencing dataset. A transcriptome sequencing dataset includes various types of gene data, including read counts ($c_i$) that are determined for each gene $g_i$, and also the number of bases per gene model, which is referred to as gene length ($x_i$, which is expressed in kilobases, or kb). The expression level ($y_i$) of a gene $g_i$ is equal to $c_i/x_i$. FIG. 2 shows a graph 200 of gene length versus expression level for example genes in a sample. Graph 200 shows rectangles corresponding to three genes 201, 202, and 203, with differing gene lengths and expression levels. The read counts of the three genes 201, 202, 203 are proportional to the areas of the respective rectangles. The respective read counts, gene lengths, and expression levels for each of genes 201, 202, 203 are given in Table 1 below. Table 1 further illustrates RPKM normalization of the data regarding genes 201, 202, 203, which is a scaled normalization.

TABLE 1

| Gene Data and Normalization | | | | |
|---|---|---|---|---|
| | Unit | Gene 201 | Gene 202 | Gene 203 |
| Per gene: read count ($c_i$) | count | 150 | 50 | 100 |
| Gene length ($x_i$) | kb | 5 | 1 | 5 |
| Expression ($y_i = c_i/x_i$) | count/kb | 30 | 50 | 20 |
| $M = \Sigma_i c_i$ | count | | $300 = 0.0003 \times 10^6$ | |
| Normalized gene expression ($z_i = y_i/M$) | 1/kb | 1/10 | 1/6 | 1/15 |
| Gene RPKM$_i$ ($z_i \times 10^6$) | 1/kb | $(1/10) \times 10^6$ | $(1/6) \times 10^6$ | $(1/15) \times 10^6$ |

The number of genes $g_i$ in the dataset is N, $c_i$ is the read count of a gene $g_i$, and $x_i$ is the length in kb of gene i, for i from 1 to N. For RPKM normalization, a value $z_i$ is attributed to each gene $g_i$ assuming M is equal to 1. $\Sigma_i x_i z_i$ is therefore equal to 1 because $z_i$ is normalized. RPKM$_i$ is a value attributed to each gene $g_i$ assuming M is equal to $10^6$. The values $c_i$ and $y_i$ for each gene $g_i$ are related to RPKM$_i$ by the following relationships:

$$c_i=RPKM_i x_i M; \text{ and} \quad (EQ. 4)$$

$$y_i=RPKM_i M \quad (EQ. 5)$$

Count $c_i$ is an unscaled value, while $z_i$ and RPKM$_i$ are scaled. RPKM normalization gives a scaled value (i.e., $z_i \times 10^6$) having unit of 1/kb and depending on the total number of genes in the dataset for each gene $g_i$; the scaling may introduce distortions into differential expression analysis that is performed using the RPKM values.

It should be noted that input datasets obtained by the transcriptome sequencing data analyzer 109, in one embodiment, include datasets from at least two experiments, while one or more additional dataset replicates can be simulated from those input datasets. For example, additional replicate datasets can be generated by sampling repeatedly from an input dataset's expression abundance distribution. In this embodiment, an estimation of the distribution of the random variables $X_g$ of EQ. 1 is performed by the transcriptome sequencing data analyzer 109 as follows.

Let $c=(c_{g_1}, c_{g_2}, \ldots, c_{g_L})$ be the observed abundances in the experiment. Without loss of generality, let $c_g$ be the number of reads (read-counts) of gene g, and $E_{g \in G} c_g = M$. To estimate the distribution a Bernoulli process with parameters $c_g/M$, for $g \in G$, and M is used. This is a natural extension of the method for the single replicate. Let $(c_g^1)_{g \in G}$, $(c_g^2)_{g \in G}, \ldots, (c_g^k)_{g \in G}, \ldots, (c_g^K)_{g \in G}$ be the observed abundances in the K experiments under identical conditions. Let $c_g^k$ be the number of reads (read-counts) of gene g in the k th replicate, for $1 \leq k \leq K$. Let $M^k = \Sigma_g c_g^k$. K Bernoulli processes each with parameters $c_g^k/M^k$ are used, for $g \in G$, and $M^k$, as in the single replicate case. Let $c_g = \Sigma_{k=1}^K c_g^k$ and let $M = \Sigma_g c_g$. The probability, $p_g$, of gene g is estimated to be $c_g/M$.

Thus, modeling the experiment, with $K \geq 1$ replicates, as a Bernoulli process, $T=(X_g)_{g \in G}$ of EQ. 1 follows a multinomial distribution with parameters M and $(p_g)_{g \in G}$. In one embodiment, a closed form of the distribution of $\phi_g$ is not straightforward to estimate and moreover, the argument to $\phi_g$ is an L-tuple $t \in R_{\geq 0}^G$. Therefore, one or more embodiments simulate the Bernoulli process. Then based on the definition of the character functions discussed above, for a fixed P, $\phi_g$ is evaluated for each g using the L -tuple, $t_i$, of trial i.

In one embodiment, the transcriptome sequencing data analyzer 109 simulates the Bernoulli process as follows. The simulation process is discussed below, for some number of iterations I (e.g., $I=10^3$), and some number of reads R (e.g., $R=10^7$), using a fixed P (e.g. P=20). Consider iteration i, the transcriptome sequencing data analyzer 109 repeats the following for each read $r \in R$: choose a replicate $k \in K$ based on the probabilities $p^k = M^k/\Sigma_{i=1}^K M^i$, and assign the read to gene $g \in G$ with probability $p_g^k = \log c_g^k/\Sigma_{i=1}^L \log c_i^k$. The transcriptome sequencing data analyzer 109 then orders genes according to decreasing assigned read count, assign $\phi_q^i = 1$ for any genes g with 0 reads. The transcriptome sequencing data analyzer 109 applies linear segmentation with P-1 segments to the cumulative sum of the ordered read counts; assign $\phi_g^i = P$ for genes g in the first segment, P-1 for the second segment, and so forth. Least-squares linear segmentation can be performed in time $O(n^2P)$. When n is large subsampling of the genes can be performed, e.g., only use every 10th gene for the segmentation.

The values $\phi_g^i$ are stored in each iteration i and together make up the distributions $\phi_g(T^a)$, while the entire distribution for dataset a is denoted $\phi(T^a)$. The values of the dispersion function $\psi_p$ are computed using the distributions $\phi_g$. In one embodiment, the number of pairs of iterations (i, i') $\in (1 \ldots I, 1 \ldots I)$ are counted to compute $Pr(\psi_p(\Phi^b|\Phi^a) = q)$, where $\phi_g^{a_i} = p$ and $\phi_g^{b_{i'}} = q$, and where $\phi_g^{a_i}$ denotes the value of gene g in iteration i in dataset a. The probability Pr is the frequency of pairs $(\phi_g^{a_i} = p, \phi_g^{b_{i'}} = q)$ among all the pairs $(\phi_g^{a_i} = p, \phi_g^{b_{i'}} = p' \in 1 \ldots P)$.

Once the transcriptome sequencing data analyzer 109 obtains the plurality of input datasets one or more rank normalization operations are performed on the input dataset's genes' expression abundance (or on the datasets generated by sampling repeatedly from the input dataset's expression abundance distribution). Rank normalization, which gives an unscaled unit-free value for each gene that may be used to perform stable gene analysis, can be performed based on $c_i$ and/or $y_i$ values for each gene $g_i$ in various embodiments. For example, rank normalization, in one embodiment, is performed by ordering the genes within each dataset based on a ranking value, and each gene is assigned a ranking relative to the other genes in the same data set. In various embodiments, the ranking value may be the read count ($c_i$) or expression level ($y_i$) values for the genes, which are unscaled values. In further embodiments, the ranking value may be the value of $\log(c_i)$ or $\log(y_i)$, as $\log(c_i)$ and $\log(y_i)$ maintain the same order of the genes as ordering by $c_i$ or $y_i$. In various embodiments, the genes may be ranked from lowest to highest, or from highest to lowest. Each gene $g_i$ is assigned a rank $r_i$. In some embodiments, $r_i$ is a unique value from 1 to N, where N is the number of genes $g_i$ in the sample. In other embodiments, rank normalization may be performed based on binning, which is discussed below with respect to FIG. 4.

The transcriptome sequencing data analyzer 109 utilizes the rank normalized input datasets (or rank normalized sampled instances of input datasets) to identify stable genes. It should be noted that while the abundances of the genes across $T^a$ and $T^b$ on the same gene set G provide a framework for detecting differentially expressed genes, the same is not adequate to determine the stable or non-changing (non-DE) genes in G. Therefore, the transcriptome sequencing data analyzer 109, in one embodiment, utilizes a combinatorial framework inspired by the $\Phi$ character functions, whose image is a set of positive integers, to detect the stable genes based on the rank normalized input datasets.

Let $\pi = p_1, p_2, \ldots, p_l$ be a sequence of positive integers. Further, $\text{len}(\pi) = l$ is the length of $\pi$ and its i th element, $p_i$, is also written as $\pi(i)$. A sequence $\pi' = p_{i_1}, p_{i_2}, \ldots, p_{i_{l'}}$, for some $i_1 < i_2 < \ldots < i_{l'}$ and $l' \leq l$, is called a subsequence of $\pi$. Further, if $p_{i_1} \leq p_{i_2} \leq \ldots \leq p_{i_{l'}}$ holds then it is called an increasing subsequence. For example, consider the sequences $\pi_1 = 112111232223$,
$\pi_2 = 111112222233$,
$\pi_3 = 11111123$, and,
$\pi_4 = 1112222$.

Here, $\pi_4$ is a subsequence of both $\pi_1$ and $\pi_2$, but not $\pi_3$; $\pi_3$ is not a subsequence of any of the other three; $\pi_2$, $\pi_3$ and $\pi_4$ are increasing sequences.

Consider $\phi^a$ and $\phi^b$ of EQ. 3. Let $\pi^a$ be an increasing sequence with a one-to-one map $$\theta: \{1, 2, \ldots, L\} \to \{g_1, g_2, \ldots, g_L\} \qquad (EQ. 6)$$

such that $\pi^a(i) = \phi^a(\theta(i))$. Based on $\pi^a$, $\pi^b$ is defined as follows: for $1 \leq i \leq L$, $\pi^b(i) = \phi^b(\theta(i))$. Notice that, in effect, $\pi^b$ is a re-labeling of $\phi^b$ in terms of $\phi^a$. Consider the following example with at least two possible $\theta$ maps, $\theta_1$ and $\theta_2$, and their corresponding sequences $\pi^a$ and $\pi^b$.

| | | i | 123456 | i | 123456 |
|---|---|---|---|---|---|
| $\phi^a =$ | 211243 | $\theta_1$ (i) | 231465 | $\theta_2$ (i) | 324165 |
| $\phi^b =$ | 141321 | $\pi^a =$ | 112234 | $\pi^a =$ | 112234 |
| | | $\pi^b =$ | 411312 | $\pi^b =$ | 143112 |

Next, a stable set of $\phi^a$ and $\phi^b$ is modeled as a longest increasing subsequence (LIS) of $\pi^b$. This problem is defined as follows: given an integer sequence $\pi$, let $\Pi$ be the set of all increasing subsequences of π. Then π' is a longest increasing subsequence of π if and only if len(π')=max{len (π")|π" ∈ Π}. The LIS problem can be solved exactly in polynomial time. For example, the LIS problem can be solved exactly in time O(n log n) using dynamic programming. However, when keeping track of all possible alternative LIS solutions the time complexity becomes O(n²+N), where N is the number of alternative LIS solutions.

Two distinct subsequences π' and π" are mutually longest increasing subsequences if len(π')=len(π") and the subsequences are increasing. In the worst case, the number N of alternative LIS solutions is exponential, i.e. (O(1))ⁿ, for a sequence of length n. Consider the following example: π=13246579810121113154 . . . n. Then it can be verified that all the O(2ⁿ) maximal LIS are obtained by iterating over all combinations by picking one entry from the two elements in each of the square brackets: 1[3, 2]4[6,5]7[9,8]10[12,11]13[15,14] . . . n.

Dynamic programming relies on the fact that the LIS solutions for the prefixes of sequence S can be utilized when computing the LIS for S. The transcriptome sequencing data analyzer 109 iteratively finds the LIS ending at position i, i=1, 2, . . . , n, where n is the number of elements in sequence S. Sequence S is the re-labeled sequence $\pi^b$ in the case of stable genes.

The maximum size of a LIS ending at position j is denoted as $M_j$. When processing element $S_i$, the transcriptome sequencing data analyzer 109 checks all the thus far largest $M_j$, j<i, for which $S_i \geq S_j$ and extends their LIS with $S_i$. There may exist several j with the same size $M_j$, and they are each examined as possible alternative solutions. Consider for example a pathological case S=7, 6, 5, 3, 2, 1, 4. The LIS size for S is 2 and the possible solutions are (3,4), (2,4), (1,4). When considering the last element $S_n$=4, the transcriptome sequencing data analyzer 109 finds all the positions j<n with the maximal $M_j$ (in the example maximal $M_j$=1, j=1, . . . , 6). The elements $S_4$, $S_5$, $S_6$ are linked to $S_n$ as potential prefixes of the LIS ending at position n (since they are no greater than $S_n$).

Searching for the maximum $M_j$ with $S_i \geq S_j$ can be done in time O(log n) when storing the values in a sorted data structure. The transcriptome sequencing data analyzer 109 generates at most n−1 links to prefixes $S_j$ for each position i=1, . . . , n. Therefore the computational complexity of this algorithm utilized by the transcriptome sequencing data analyzer 109 for computing all the possible solutions to the LIS problem becomes O(n² log n), or simply O(n²) when the search is omitted and all positions j<i are considered for each i=1, . . . , n. In practice there may exist few alternative solutions and using a binary search option can be used. However, the output size N may be exponential, so in the worst case an algorithm that outputs all possible LIS solutions takes time O(n²)+(O(1))ⁿ.

Based on the above, the transcriptome sequencing data analyzer 109 selects a set of stable genes from the one or more longest increasing subsequences of each normalized input dataset. For example, consider Table 2 below, which shows ranking values for the three genes of FIG. 2 in two experiments, E1 and E2.

TABLE 2

Example Gene Rankings in two experiments.

| unit | | gene 201 | gene 202 | gene 203 |
|---|---|---|---|---|
| Rank Values in Experiment E1 | | | | |
| $c_i$ | $r_i$ | 3 | 1 | 2 |
| $y_i$ | $r_i$ | 2 | 3 | 1 |
| Log($c_i$) | $r_i$ | 3 | 1 | 2 |
| Log($y_i$) | $r_i$ | 2 | 3 | 1 |
| Rank Values in Experiment E2 | | | | |
| $c_i$ | $r_i$ | 1 | 2 | 3 |
| $y_i$ | $r_i$ | 2 | 1 | 3 |
| Log($c_i$) | $r_i$ | 1 | 2 | 3 |
| Log($y_i$) | $r_i$ | 2 | 1 | 3 |

It should be noted that the various embodiments of ranking schemes using different ranking values may order the three genes differently, as shown; therefore, the same ranking scheme is applied across datasets that are compared to one another for determination of stable genes.

When using the $c_i$ (or Log($c_i$)) rank values, the transcriptome sequencing data analyzer 109 determines that the largest set of stable genes contains genes 202 and 203, using one or more of the embodiments discussed above for determining stable genes between a pair of experiments. However, when using the $y_i$ (or Log($y_i$)) rank values, the largest set of stable genes consists only of a single gene, either gene 201, gene 202, or gene 203, since the order of the gene rank values are exactly reversed between the experiments E1 and E2.

It should be noted that in one embodiment, the transcriptome sequencing data analyzer 109 selects a set of stable genes that are present in the B longest increasing subsequences between rank normalized input datasets (or between rank normalized sampled replicate instances of input datasets). In some instances there can be several increasing subsequences with the same (longest possible) size, thus all are LIS (i.e., the LIS is not unique). Also, one or more embodiments can consider some suboptimal increasing subsequences to obtain a more robust solution, by either taking union or intersection of best e.g. B=100 solutions. Here "best" refers to the longest (increasing subsequence). For example if there are 30 solutions with the longest size L (i.e. LIS is non-unique with 30 alternative solutions), and there are 70 solutions with 2nd longest size L−1, then B=100 indicates all the solutions with length L and length L−1 are considered. The transcriptome sequencing data analyzer 109 can either take the union or intersection or do some other process on the solutions to extract the stable genes among the alternative solutions.

Figure 3:
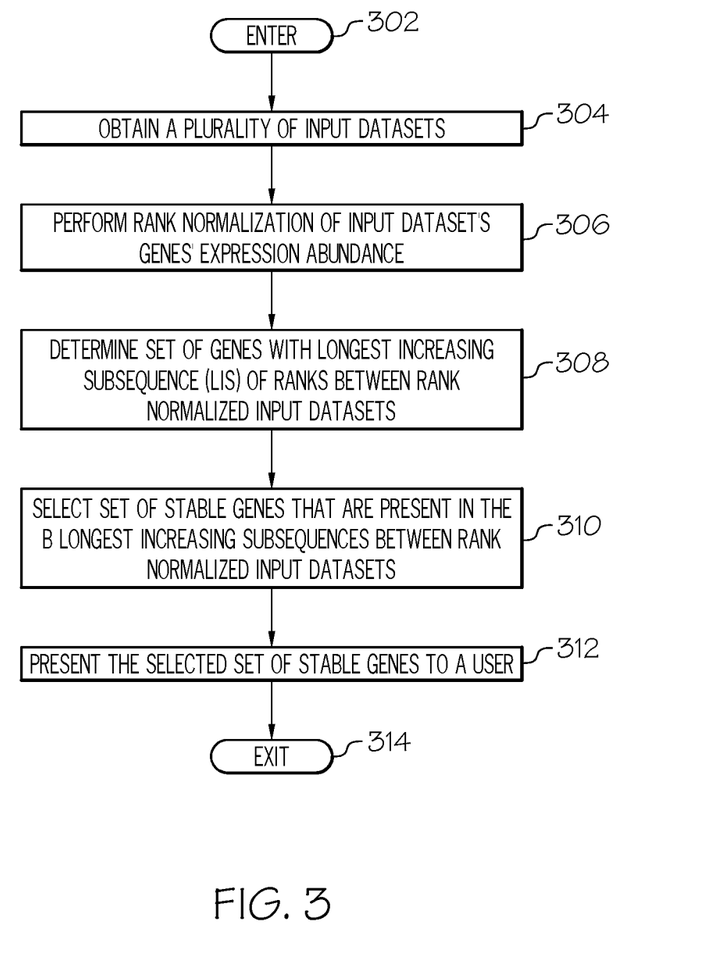
FIG. 3 is an operational flow diagram illustrating one example of an overall process for performing stable gene analysis of transcriptome sequencing data according to one embodiment of the present invention.

FIG. 3 is an operational flow diagram illustrating one example of an overall process for identifying stable genes from transcriptome sequencing data. The operational flow diagram begins at step 302 and flows directly to step 304. The transcriptome sequencing data analyzer 109, at step 304, obtains a plurality of input datasets. In one embodiment, each dataset includes transcriptome sequencing data. Each dataset can come from separate experiments or from a single dataset from a given experiment.

The transcriptome sequencing data analyzer 109, at step 306, performs rank normalization of the expression abundance of each gene in each input dataset. The transcriptome sequencing data analyzer 109, at step 308, determines/identifies a set of genes with the LIS of ranks between the rank normalized input datasets (or between rank-normalized sampled instances of input datasets). The transcriptome sequencing data analyzer 109, at step 310, selects the set of stable genes that are present in the longest B increasing subsequences between the rank normalized input datasets (or between rank-normalized sampled instances of input datasets). The transcriptome sequencing data analyzer 109, at step 312, presents the selected set of stable genes to a user. The control flow exits at step 314.

Figure 4:
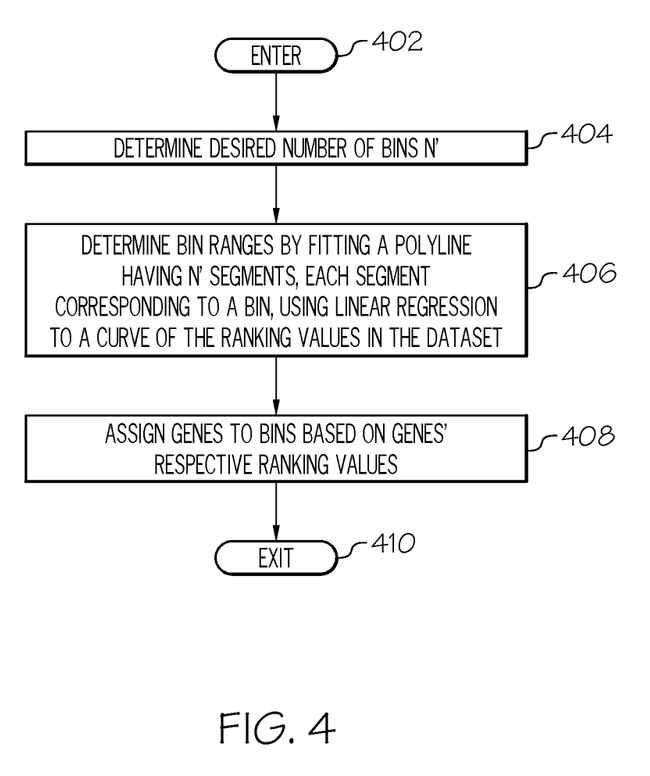
FIG. 4 is an operational flow diagram illustrating one example of a process for performing rank normalization as part of the process illustrated in FIG. 3 according to one embodiment of the present invention.

FIG. 4 is an operational flow diagram illustrating a more detailed example of performing rank normalization (step 306 of FIG. 3). The operational flow diagram begins at step 402 and flows directly to step 404. Genes with similar ranking values may be deemed rank-indistinguishable. Therefore, instead of assigning a unique rank to each gene $g_i$ as was discussed above, the genes may be assigned to bins, or ranges, such that all genes assigned to a single bin are assigned the same rank $r_i$. In this embodiment, transcriptome sequencing data analyzer 109, at step 404, determines a desired number of bins N' for each dataset. N' may be determined based on the number of genes N in a dataset.

The transcriptome sequencing data analyzer 109, at step 406, utilizes linear regression to fit a polyline with N' linear segments to a cumulative curve of a graph of the ranking values (i.e., $c_i$, $y_i$, log ($c_i$), or log ($y_i$)) in the dataset. Each linear segment of the polyline corresponds to a bin having a range of values of the ranking value. In some embodiments, the value of N may be in tens or hundreds of thousands whereas N' may be a much smaller number, for example, of the order or tens to hundreds (i.e., N'<<N). The transcriptome sequencing data analyzer 109, at step 408, assigns each gene in a dataset to the appropriate bin based on ranking value. A rank $r_i$ for each gene $g_i$ is determined based on the bin number of the assigned bin of each gene $g_i$. For example, all genes in a bin $b_k$, where k goes from 1 to N', are assigned the same rank $r_i$ that is equal to k. The control flow then exits at step 410.

Figure 5:
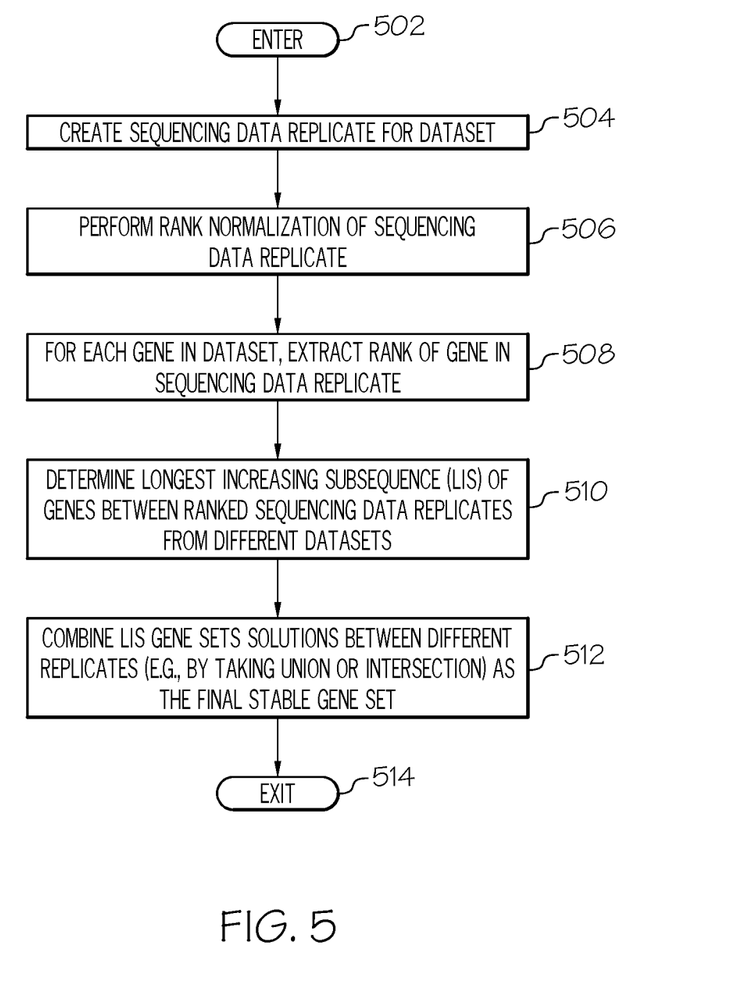
FIG. 5 is an operational flow diagram illustrating one example of a process for determining/detecting stable genes as part of the process illustrated in FIG. 3 according to one embodiment of the present invention.

FIG. 5 is an operational flow diagram illustrating a more detailed example of determining/detecting stable genes (step 308 of FIG. 3). The operational flow diagram begins at step 502 and flows directly to step 504. It should be noted that the following discussion is with respect to replicate input datasets generated by sampling repeatedly from an input dataset's expression abundance distribution. However, this discussion is also applicable to datasets from different experiments as well.

The transcriptome sequencing data analyzer 109, at step 504, creates transcriptome sequencing data replicate $S'_j$. The replicate is created such that the cumulative read count curve of $S'_j$ matches that of the given sample S by sampling on the cumulative curve of S. The transcriptome sequencing data analyzer 109, at step 506, performs rank normalization of the data in $S'_j$ as was discussed above. For embodiments in which gene ranks in S were assigned based on binning as was discussed with respect to FIG. 4, the same binning scheme that was used for S is used in the replicate $S'_j$. The transcriptome sequencing data analyzer 109, at step 508, extracts, for each gene in S with a rank r, the rank $r'_j$ for the gene in $S'_j$. The transcriptome sequencing data analyzer 109, at step 510, determines the LIS of genes between ranked sequencing data replicates from different datasets. The transcriptome sequencing data analyzer 109, at step 512, combines LIS gene set solutions between different replicates as the final stable gene set. The combining of LIS gene sets can be performed, for example, by either taking the union or intersection of the LIS gene set solutions between different replicates. The control flow then exits at step 514.

NON-LIMITING EXAMPLES

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems), and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for optimizing at least one computing system when performing stable gene analysis of transcriptome sequencing data, wherein the method comprises:
    adding, by a processor of at least one computing system, one or more replicate datasets to a plurality of datasets as separate datasets, wherein each dataset of the plurality of datasets comprises a plurality of genes and expression levels for each gene of the plurality of genes, and wherein the one or more replicate datasets increases a robustness for subsequent stable gene analysis operations;
    assigning, by the processor for each dataset of the plurality of datasets, a rank value to each gene of the plurality of genes after the one or more replicate datasets have been added to the plurality of datasets, wherein the assigning comprises:
        generating, by the processor, a plurality of bins, each bin comprising a range of values of the rank value, and
        assigning, by the processor, each gene to a bin of the plurality of bins based on the gene's respective ranking value, wherein genes that are assigned to the same bin have been assigned the same rank;
    obtaining, by the processor, a plurality of rank normalized input datasets based on the assigning, each rank normalized input dataset of the plurality of rank normalized input datasets comprising a sequence of normalized values; and
    operating on, by the processor, the plurality of rank normalized input datasets utilizing a dynamic programming process, the dynamic programming process optimizing the at least one computing system by reducing computation time required for performing the stable gene analysis of transcriptome sequencing data, wherein reducing the computation time comprises:
        iteratively identifying, for each rank normalized input dataset of plurality of rank normalized input datasets, a longest increasing subsequence of ranks at each position in the sequence of normalized values;
        storing, for each iteration, a maximum size of the longest increasing subsequence of ranks and a position within the sequence of normalized values associated with the maximum size in a sorted data structure residing within a memory of the computing system,
        wherein for each iteration subsequent to an initial iteration, the longest increasing subsequence of ranks is identified based on searching the sorted data structure for all maximum sizes associated with positions of the sequence of normalized values that precede a current position of the sequence of normalized values, and extending the longest increasing subsequence of ranks for the preceding positions with the normalized value of the current position; and
    identifying, by the processor based on each of the longest increasing subsequence of ranks, a set of stable genes from the plurality of genes.

2. The method of claim 1, wherein the plurality of datasets include a dataset associated with an expression abundance distribution, and
    wherein each remaining at least one other dataset in the plurality of datasets is generated based on sampling repeatedly from the expression abundance distribution of the dataset.

3. The method of claim 1, wherein the ranking value comprises a gene count of the respective gene.

4. The method of claim 3, wherein the ranking value comprises a logarithm of the gene count of the respective gene.

5. The method of claim 1, wherein the ranking value comprises an expression level of the respective gene.

6. The method of claim 5, wherein the ranking value comprises a logarithm of the expression level of the respective gene.

7. The method of claim 1, wherein the plurality of bins is determined based on fitting a polyline, the polyline comprising a plurality of segments, by linear regression to a graph of the ranking values of each of the plurality of datasets, wherein each of the plurality of segments corresponds to a bin of the plurality of bins.

8. The method of claim 1, wherein the one or more replicate datasets are obtained by performing one or more simulation operations on the plurality of datasets, wherein the one or more simulation operations generate the one or more replicate datasets for each dataset of the plurality of datasets.

9. The method of claim 1, wherein assigning the rank value to each gene of the plurality of genes comprises assigning a unique rank value to each gene of the plurality of genes.

10. A method for optimizing at least one computing system when performing stable gene analysis of transcriptome sequencing data, wherein the method comprises:
   obtaining, by a processor of at least one computing system, a plurality of datasets, wherein each dataset of the plurality of datasets comprises a plurality of genes and expression levels for each gene of the plurality of genes;
   assigning, by the processor for each dataset of the plurality of datasets, a rank value to each gene of the plurality of genes;
   obtaining, by the processor, a plurality of rank normalized input datasets based on the assigning, each rank normalized input dataset of the plurality of rank normalized input datasets comprising a sequence of normalized values; and
   operating on, by the processor, the plurality of rank normalized input datasets utilizing a dynamic programming process, the dynamic programming process optimizing the at least one computing system by reducing computation time required for performing the stable gene analysis of transcriptome sequencing data, wherein reducing the computation time comprises:
      iteratively identifying, for each rank normalized input dataset of plurality of rank normalized input datasets, a longest increasing subsequence of ranks at each position in the sequence of normalized values;
      storing, for each iteration, a maximum size of the longest increasing subsequence of ranks and a position within the sequence of normalized values associated with the maximum size in a sorted data structure residing within a memory of the computing system; and
      identifying, by the processor based on each of the longest increasing subsequence of ranks, a set of stable genes from the plurality of genes.

11. The method of claim 10, wherein the plurality of datasets include a dataset associated with an expression abundance distribution, and
   wherein each remaining at least one other dataset in the plurality of datasets is generated based on sampling repeatedly from the expression abundance distribution of the dataset.

12. The method of claim 10, wherein the ranking value comprises a gene count of the respective gene.

13. The method of claim 12, wherein the ranking value comprises a logarithm of the gene count of the respective gene.

14. The method of claim 10, wherein the ranking value comprises an expression level of the respective gene.

15. The method of claim 14, wherein the ranking value comprises a logarithm of the expression level of the respective gene.

16. The method of claim 10, wherein assigning the rank value to each gene of the plurality of genes comprises:
   determining a plurality of bins, each bin comprising a range of values of the ranking value; and
   assigning each gene to a bin of the plurality of bins based on the gene's respective ranking value, wherein genes that are assigned to the same bin are assigned the same rank.

17. The method of claim 16, wherein the plurality of bins is determined based on fitting a polyline, the polyline comprising a plurality of segments, by linear regression to a graph of the ranking values of each of the plurality of datasets, wherein each of the plurality of segments corresponds to a bin of the plurality of bins.

18. The method of claim 10, wherein assigning the rank value to each gene of the plurality of genes comprises assigning a unique rank value to each gene of the plurality of genes.

19. The method of claim 10, wherein for each iteration subsequent to an initial iteration, the longest increasing subsequence of ranks is identified based on searching the sorted data structure for all maximum sizes associated with positions of the sequence of normalized values that precede a current position of the sequence of normalized values, and extending the longest increasing subsequence of ranks for the preceding positions with the normalized value of the current position.

* * * * *